(12) United States Patent
Larsson et al.

(10) Patent No.: US 7,799,914 B2
(45) Date of Patent: Sep. 21, 2010

(54) CHEMICAL PROCESS

(75) Inventors: Ulf Larsson, Sodertalje (SE); Kajsa Radevik, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/599,377

(22) PCT Filed: Mar. 29, 2005

(86) PCT No.: PCT/GB2005/001188

§ 371 (c)(1),
(2), (4) Date: Sep. 27, 2006

(87) PCT Pub. No.: WO2005/095358

PCT Pub. Date: Oct. 13, 2005

(65) Prior Publication Data

US 2007/0219371 A1    Sep. 20, 2007

(30) Foreign Application Priority Data

Mar. 31, 2004    (SE) .................................. 0401001

(51) Int. Cl.
*C07D 239/38*    (2006.01)
*C07D 239/30*    (2006.01)
(52) U.S. Cl. ...................... 544/316; 544/309
(58) Field of Classification Search ................. 544/316
See application file for complete search history.

(56) References Cited

U.S. PATENT DOCUMENTS

| 6,096,924 | A | 8/2000 | Studer et al. | |
|---|---|---|---|---|
| 6,818,720 | B2 * | 11/2004 | Krauter et al. | 502/257 |
| 7,067,663 | B2 * | 6/2006 | Larsson et al. | 544/301 |

FOREIGN PATENT DOCUMENTS

| EP | 0508687 | 10/1992 |
|---|---|---|
| WO | 99/05143 | 2/1999 |
| WO | 00/34283 | 6/2000 |
| WO | 01/92263 | 12/2001 |

OTHER PUBLICATIONS

Degussa Booklet Guide for catalytic hydrogenation, p. 14, 2000.*

* cited by examiner

*Primary Examiner*—Venkataraman Balasubramanian
(74) *Attorney, Agent, or Firm*—Pepper Hamilton LLP

(57) ABSTRACT

The present invention provides a process for the preparation of a compound of formula (I):

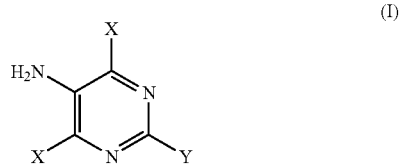

(I)

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl; the process comprising either:

a. hydrogenating a compound of formula (II):

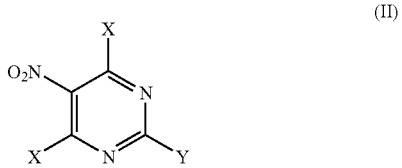

(II)

with a suitable transition metal catalyst in a $C_{1-6}$ aliphatic alcohol, an ether, an ester or a hydrocarbon as solvent;
or,
b. conducting a one-pot hydrogenation of a compound of formula (III):

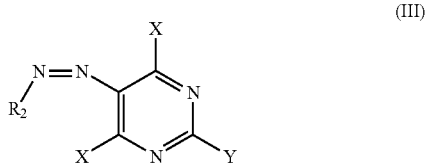

(III)

wherein $R^2$ is phenyl optionally substituted by chloro, $C_{1-6}$ alkyl, $C_{1-6}$ alkoxy or $(C_{1-6}$ alkyl$)_2$N;
  i. firstly at about 20° C. to form a compound of formula (IV):

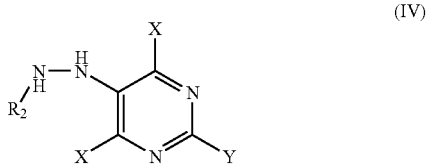

(IV)

ii. and then at about 40° C.;
both steps (i) and (ii) being carried out in the presence of a suitable catalyst and in the presence of a suitable solvent.

4 Claims, No Drawings

CHEMICAL PROCESS

CROSS-REFERENCE TO RELATED APPLICATIONS

This application is the U.S. National Stage filing of International Application Serial No. PCT/GB2005/001188 filed Mar. 29, 2005, which claims priority to Swedish Application Serial No. 0401001-3 filed Mar. 31, 2004, each of which is incorporated herein by reference in its entirety.

The present invention concerns a process fox the preparation of 5-aminopyrimidines which are useful intermediates in the preparation of pharmaceutically active triazolo[4,5-d]pyrimidine cyclopentanes.

The compound [1S-(1α,2α,3β(1S*,2R*),5β)]-3-[7-[2-(3,4-difluorophenyl-cyclopropyl]amino]-5-(propylthio)-3H-1,2,3-triazolo[4,5-d]pyrimidin-3-yl)-5-(2-hydroxyethoxy)-cyclopentane-1,2-diol (Compound A), and similar such compounds, are disclosed in WO 00/34283 and WO 99/05143 as pharmaceutically active $P_{2T}$ (which is now usually referred to as $P_2Y_{12}$) receptor antagonists. Such antagonists can be used as, inter alia, inhibitors of platelet activation, aggregation or degranulation.

Compounds of formula (I) (see below) are useful in the preparation of Compound A and analogues thereof (see example 3 of WO 01/92263).

Catalytic hydrogenation of aromatic nitro compounds is disclosed in U.S. Pat. No. 6,096,924.

The present invention provides a process for the preparation of a compound of formula (I):

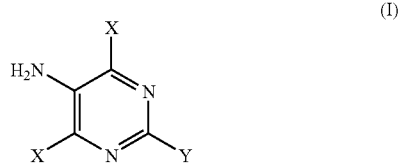

(I)

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl; the process comprising either:

a. hydrogenating a compound of formula (II):

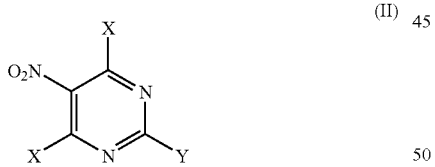

(II)

with a suitable transition metal catalyst in a $C_{1-6}$ aliphatic alcohol, an ether, an ester or a hydrocarbon as solvent;

or, b. conducting a one-pot hydrogenation of a compound of formula (III):

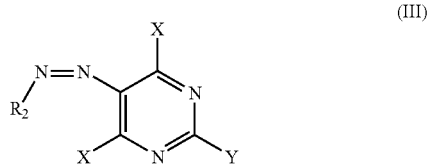

(III)

wherein $R^2$ is phenyl optionally substituted by chloro, $C_{1-6}$ alkyl, $C_{1-6}$ alkoxy or $(C_{1-6}$ alkyl$)_2$N;

i. firstly at about 20° C. to form a compound of formula (IV):

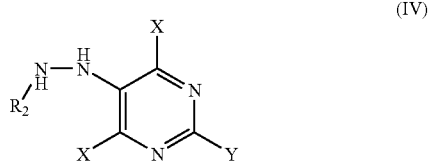

(IV)

ii. and then at about 40° C.;
both steps (i) and (ii) being carried out in the presence of a suitable catalyst and in the presence of a suitable solvent.

Alkyl groups and moieties are straight or branched chain and comprise, for example, 1 to 6 (such as 1 to 4) carbon atoms. Examples of alkyl groups are methyl, ethyl, n-propyl, iso-propyl or tert-butyl.

Haloalkyl groups and moieties are straight or branched chain and comprise, for example, 1 to 6 (such as 1 to 4) carbon atoms, and 1 to 6 halogen atoms (for example fluorine or chlorine atoms). Examples of haloalkyl are $CH_2F$, $CHF_2$, $CF_3$, $CH_2CF_3$ and 3,3,3-trifluoroprop-1-yl.

Cycloalkyl is, for example, $C_{3-6}$ cycloalkyl, such as cyclopropyl, cyclopentyl or cyclohexyl.

In one particular aspect the present invention provides a process for the preparation of a compound of formula (I):

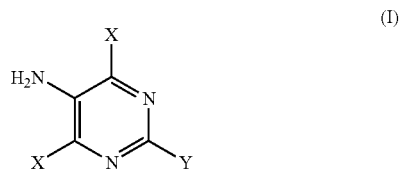

(I)

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl; the process comprising hydrogenating a compound of formula (II):

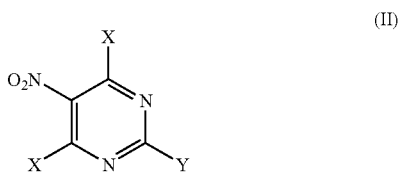

(II)

with a suitable transition metal catalyst in $C_{1-6}$ aliphatic alcohol, an ether, an ester or a hydrocarbon as solvent.

Suitable transition metal catalyst for the hydrogenation of a compound of formula (II) is, for example, platinum or palladium, or a combination of platinum with another transition metal such as vanadium, iron or manganese. In a further aspect of the invention the transition metal catalyst is on a suitable support, for example carbon.

A suitable solvent for the hydrogenation of a compound of formula (II) is a $C_{1-6}$ aliphatic alcohol (such as ethanol and iso-propyl alcohol), an ether (for example a di($C_{1-6}$ alkyl) ether, such as diethylether or methyl tert-butyl ether; or a cyclic ether such as tetrahydrofuran), an ester (for example ethyl acetate) or a hydrocarbon solvent (such as an aromatic hydrocarbon, for example benzene, toluene or a xylene).

In another aspect the hydrogenation of a compound of formula (II) is conducted at a temperature in the range 10 to 90° C., for example 20 to 40° C.

In yet another aspect the hydrogenation of a compound of formula (II) is conducted at a pressure of 1 to 10 bar, for example 2 to 4 bar.

In a further aspect the present invention provides a process for the preparation of a compound of formula (I):

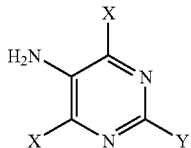

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl; the process comprising conducting a one-pot hydrogenation of a compound of formula (III):

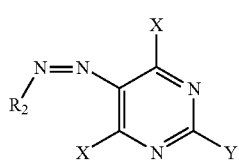

wherein $R^2$ is phenyl optionally substituted by chloro, $C_{1-6}$ alkyl, $C_{1-6}$ alkoxy or $(C_{1-6}$ alkyl$)_2$N;
i. firstly at 10 to 25° C. to form a compound of formula (IV):

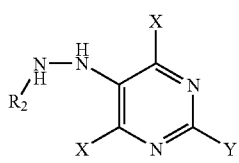

ii. and then hydrogenating at about 35 to 50° C.;
both steps (i) and (ii) being carried out in the presence of a suitable catalyst and in the presence of a suitable solvent.

Highly effective mixing (for example stirring) is used during the one-pot hydrogenation as this aids effective mass transfer during the process. Highly effective mixing is used to obtain good contact between the gaseous hydrogen, the solid catalyst and the compound of formula (III) or (IV).

A suitable catalyst for the one-pot hydrogenation is either a single transition metal or a mixture of two or more transition metals. Suitable catalysts are platinum or a mixture of platinum and vanadium. It is usual for the catalyst to be on a suitable support (for example carbon). Examples of these catalysts are platinum on carbon 5-15% w/w; platinum 2-10% w/w (for example 3-7% w/w) and vanadium 0.2-3% w/w on carbon.

A suitable solvent for the one-pot hydrogenation is a $C_{1-6}$ aliphatic alcohol (for example ethanol or iso-propyl alcohol), an ester (for example ethyl acetate), an ether (such as tetrahydrofuran or methyl tert-butyl ether), a hydrocarbon (such as an aromatic hydrocarbon, for example benzene, toluene or a xylene) or a ketone (such as acetone).

In yet another aspect the hydrogenation of a compound of formula (III) or (IV) is conducted at a pressure of 0.5 to 10 bar, for example 2 to 4 bar.

In a still further aspect the present invention provides a process as hereinbefore described wherein X is chloro.

In another aspect the present invention provides a process as hereinbefore described wherein Z is sulphur.

In yet another aspect the present invention provides a process as hereinbefore described wherein $R^1$ is $C_{1-4}$ alkyl (such as n-propyl) or $C_{1-4}$ haloalkyl (such as 3,3,3-trifluoroprop-1-yl).

In yet another aspect the present invention provides a process as herein described where in 5-15% w/w catalyst is used based on compound of formula (II) or (III).

The following Examples illustrate the invention.

EXAMPLE 1

This Example illustrates a process for the preparation of 4,6-dichloro-2-(propylthio)pyrimidin-5-amine.

A Pt/V/C catalyst (available from Degussa; about 3% Pt and 0.6% V adsorbed on charcoal, 30 g) was charged to a vessel and the vessel was purged with nitrogen. 4,6-Dichloro-5-nitro-2-(propylthio)pyrimidine (302 g) dissolved in tert-butyl methyl ether (3 l) was charged to the vessel and agitation was started. The resulting mixture was heated to an initial temperature of 30° C. and then the vessel was pressurized with hydrogen to 3 bar for 3 hours. After the completion of the hydrogenation the catalyst was filtered off. The filtrate was concentrated under reduced pressure to provide the title compound (254 g).

EXAMPLE 2

This Example illustrates a process for the preparation of 4,6-dichloro-2-(propylthio)pyrimidin-5-amine from 4,6-dichloro-5-[(E)-(4-methylphenyl)diazenyl]-2-(propylsulfanyl)pyrimidine

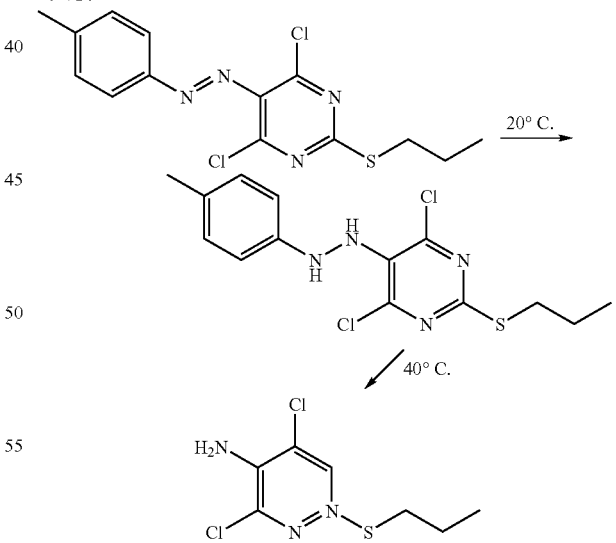

The Pt/C catalyst (33.3 g, 10% w/w) was added to a reaction vessel that had been purged with nitrogen and maintained under an atmosphere of nitrogen. The solution of 4,6-dichloro-5-[(E)-2-(4-methylphenyl)diazenyl]-2-(propylsulfanyl)pyrimidine (150 g, 430.1 mmol) in ethyl acetate (3000 ml) was added to the reaction vessel containing the catalyst and agitation was initiated. The inner temperature was adjusted to 20° C., the nitrogen atmosphere was evacuated, and the vessel was pressurized with 3 bar of hydrogen (hydrogen pressure of 3 bar was maintained throughout the reaction). The temperature was maintained at 20° C. for about 30 minutes and then it was increased to 40° C. and maintained for 150 minutes. When the reaction was complete (full conversion) the reaction solution was cooled to 20° C. and the catalyst filtered off under a nitrogen atmosphere. The catalyst was washed with ethyl acetate (300 ml) and the filtered wash-solution was combined with the filtered reaction solution. The ethyl acetate solution was concentrated to 5 ml (ethyl acetate)/g (amine) under vacuum at a maximum temperature of 40° C. The resulting solution was extracted twice with aqueous hydrochloric acid (about 3M; 700 ml and 375 ml) until a pH of 1.5-2 was obtained. The concentration of the ethyl acetate layer, under vacuum, yielded about 93 g of the 4,6-dichloro-2-(propylthio)pyrimidin-5-amine as a yellow oil.

The invention claimed is:

1. A process for the preparation of a compound of formula (I):

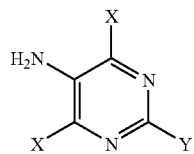

wherein:

X is chloro;

Y is $ZR^1$;

Z is sulphur; and $R^1$ is n-propyl;

the process comprising hydrogenating a compound of formula (II):

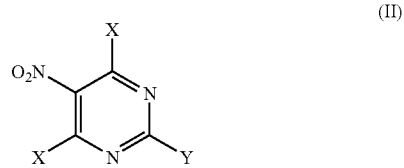

in a solvent comprising an ether, at a pressure of 2 to 4 bar, a temperature in the range 20° C. to 40° C., an in the presence of a Pt/V/C catalyst.

2. A process as claimed in claim 1 wherein the Pt/V/C catalyst comprises about 3% Pt and 0.6% V.

3. A process as claimed in claim 1 wherein the solvent is tert-butyl methyl ether.

4. A process as claimed in claim 2 wherein the solvent is tert-butyl methyl ether.

* * * * *